United States Patent [19]

Stednitz

[11] Patent Number: 4,537,185
[45] Date of Patent: Aug. 27, 1985

[54] CANNULATED FIXATION SCREW

[75] Inventor: Denis P. Stednitz, 209 Via Pasqual, Redondo Beach, Calif. 90017

[73] Assignee: Denis P. Stednitz, Redondo Beach, Calif.

[21] Appl. No.: 502,924

[22] Filed: Jun. 10, 1983

[51] Int. Cl.³ .............................................. A61F 5/04
[52] U.S. Cl. .................. 128/92 B; 128/92 EB; 128/92 A
[58] Field of Search ............ 128/92 B, 92 BB, 92 EB, 128/92 BA, 92 BC, 92 E, 92 D, 92 R, 92 A, 92 G

[56] References Cited

U.S. PATENT DOCUMENTS

| | | | |
|---|---|---|---|
| 2,242,003 | 5/1941 | Lorenzo | 128/92 BB |
| 2,388,482 | 11/1945 | Haynes | 128/92 A |
| 2,526,959 | 10/1950 | Lorenzo | 128/92 BB |
| 2,570,465 | 10/1951 | Lundholm | 128/92 BB |
| 3,554,193 | 1/1971 | Konstantinov et al. | 128/92 BB |
| 4,175,555 | 11/1979 | Herbert | 128/92 B |
| 4,341,206 | 7/1982 | Perrett et al. | 128/92 EB |
| 4,414,966 | 11/1983 | Stednitz | 128/92 B |
| 4,432,358 | 2/1984 | Fixel | 128/92 B |
| 4,450,835 | 5/1984 | Asnis et al. | 128/92 BB |
| 4,463,753 | 8/1984 | Gustilo | 128/92 B |

FOREIGN PATENT DOCUMENTS 191050  1/1967  U.S.S.R. ........................ 128/92 BA

Primary Examiner—Gene Mancene
Assistant Examiner—C. W. Shedd
Attorney, Agent, or Firm—Hubbard & Stetina

[57] ABSTRACT

A self-tapping, self-drilling orthopedic fixation screw includes a cannula through the shaft of the screw for placement over a guide pin mounted in a guide hole in a bone to drill and tap a hole at predetermined location in the bone.

1 Claim, 7 Drawing Figures

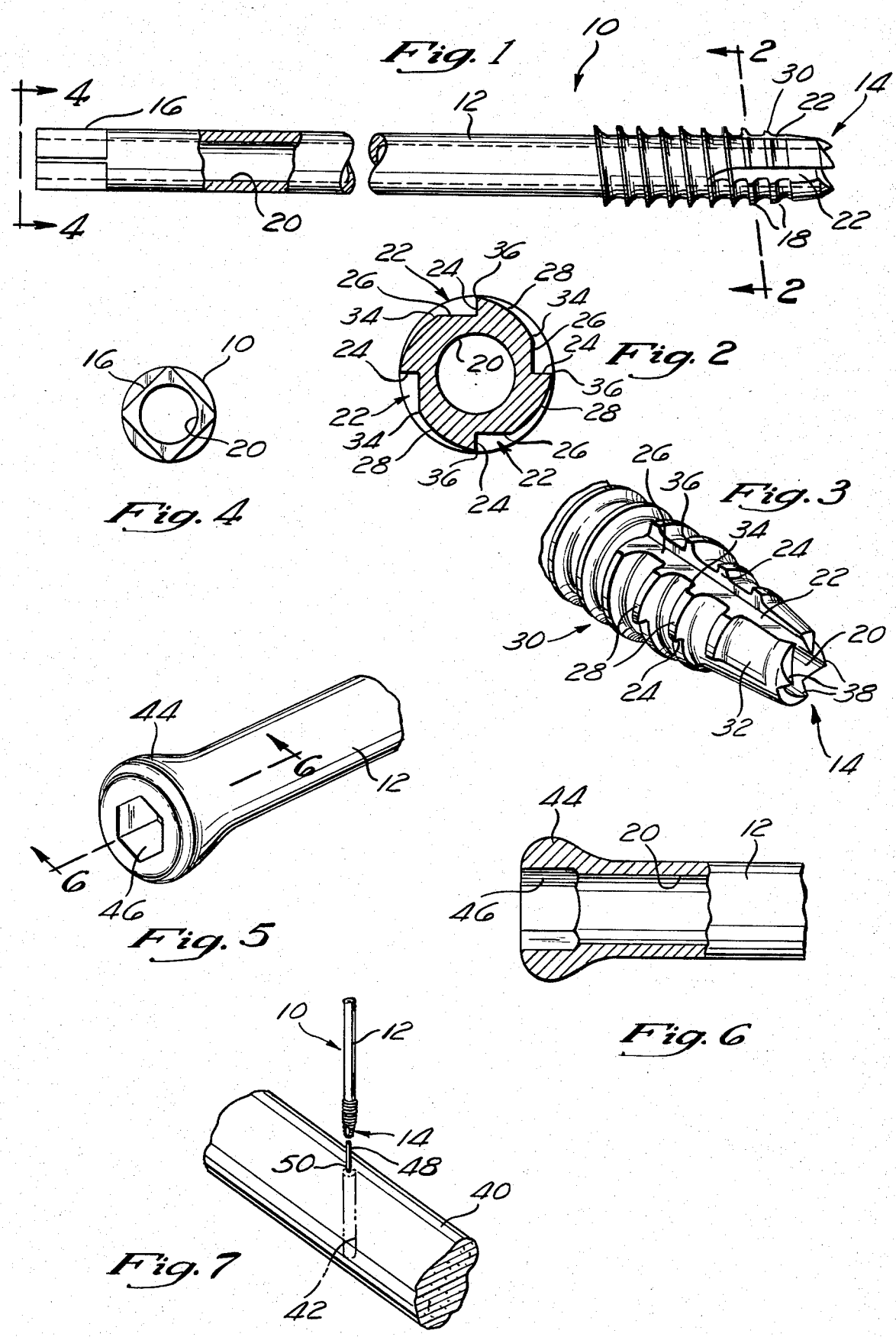

CANNULATED FIXATION SCREW

BACKGROUND OF THE INVENTION

This invention relates generally to orthopedic surgical devices and particularly to fixation screws for stabilizing factured bones.

External fixation devices using pins extending into or through bone fragments are generally accepted and widely used throughout the world. The present invention provides an improved fixation screw suitable for use with conventional external devices.

Early fixation pins were smooth, cylindrical shafts which were passed through pre-drilled holes. These pins made no screw and thread type engagement to the bone.

Later, pins were developed which were self-drilling and self-tapping. These pins were smooth, cylindrical shafts with the points matched into a pointed spade configuration which formed the drill tip, having two flat inclined surfaces on opposite sides of the longitudinal axis, and a point wedge-shaped, spade surface with knife edges that scraped away the bone when the shaft was turned.

On the self-drilling, self-tapping pin, a self-tapping thread was started at a point approximately half-way up the shallow sloping surfaces. This self-tapping thread continued up the shaft for a distance sufficient to pass through the bone for which the pin was designed.

Self-drilling, self-tapping screws have several disadvantages. First, the knife edge of the drill point is not very sharp. Consequently, the drill advances at a relatively slow speed through the bone. This slow speed was generally slower than the speed with which the self-tapping thread would advance if the hole were pre-drilled before attempting to tap the pin into the bone. This speed differential caused the thread portion to strip out the threads just cut in the bone because of the inability to advance as fast as the self-tapping thread would normally advance.

A second disadvantage is that the relatively slow speed of drilling achieved by this structure resulted in higher temperatures from friction heating of the bone surrounding the hole. Since bone is a living structure, it dies when overheated. Clinical testing has shown that when bone cells are heated to a temperature of about 105° Fahrenheit, they die. As a result, after such a pin was placed in the bone, often a small plug of bone around the hole would subsequently die. As a result, it frequently happened that a small plug of bone with the pin attached would fall out. New and painful treatment was thus necessitated for the patient.

Self-penetrating and pre-drilled screws are known. The self-penetrating types generally have a sharp point on the tip of the screw similar to self-penetrating wood screws. These self-penetrating screw structures could not be used in orthopedic work because the hardness and thickness of the bone portion surrounding the marrow would not permit the screw to penetrate absent a drilling point on the tip of the screw.

In fixing a broken bone with a fixation screw, the orthopedic surgeon must pass a fixation screw through the bone table on one side of the marrow, pass the screw through the marrow and then must find the hole in the bone table on the other side of the marrow with the tip of the screw. All of these procedures must be done by feel with the physician unable to see the holes drilled in the bone. Since the interior surfaces of the bone table facing the marrow tend to be porous, if a sharp point were used on the far side of the marrow would be more difficult because of the difficulty of sliding a sharp point over a porous surface. Generally pre-drilled, self-tapping screws utilize truncated conical surfaces at their points. These truncated surfaces have sharp edges which could catch on the porous internal bone surfaces facing the marrow when attempting to slide the fixation pin over the surface in search of the far-side hole.

In addition, such pre-drilled, self-tapping screws generally utilize only one flute cut in the tip to give a cutting edge to the helical rib of the thread. Where only one flute is used, there are unbalanced cutting forces generated as the helical rib cuts a helical groove in the bone. These forces would create very large pressures pressing the screw shaft against the bone at a point diagonally opposite the flute. These large pressures could cause damage to the bone material. Hence, the use of a structure causing balance cutting forces is preferable.

Placing a large screw in a predetermined position in a bone presents added difficulties because the point of the screw tends to slide across the outer surface of the bone. In many applications, it is difficult to ascertain the exact location of the tip of a large bone screw.

SUMMARY OF THE INVENTION

The present invention, in its exemplary and preferred form, is a cannulated orthopedic fixation screw which is adapted to be threadably attached, adjacent the distal end thereof, with a bone of the user patient, and to be attached to a fixation frame, of any desired type, adjacent to the proximal end thereof. The screw comprises an elongate cylindrical shaft having threads formed at the distal end thereof for attachment to the bone. A cannula extends through the center of the shaft. Threads are formed on the screw from the tip portion onto the shaft for a desired distance along the shaft. Self-tapping, self-drilling, cutting edges of the threads are formed on the distal end of the shaft by means of at least two flutes formed in the portions, and preferably extending into the shaft portion. Each of the flutes is defined by first and second surfaces. The first surface of the flute is generally planar and lies substantially in coincidence with a diameter of the shaft, i.e., the plane of the first surface lies on a diameter of the shaft, or lies at least substantially in the plane of the diameter of the shaft.

The second surface is generally perpendicular to the first surface and is longitudinally generally co-extensive therewith. The first surface extends from the tip of the screw longitudinally in the direction of the proximal end of the shaft to terminate in a curved portion.

The flutes are substantially symmetrically arranged about the axis of the shaft, and are so configured and constructed as to nonfluted spaces, or lands, between the respective flutes. In the preferred embodiment shown in the exemplary drawings, there are four flutes and four nonfluted spaces therebetween. The nonfluted surfaces between the flutes intersect the first surface of the flute adjacent to form a cutting surface in the thread configuration, thereby resulting in a self-tapping cutting the ends of the flutes have portions cut therefrom to form sharp cutting points on the second surfaces forming the flutes.

In the nonfluted regions between the flutes, the thread depth decreases from the second surfaces to the first surfaces. Such threads have cutting edges having acute angles at the flutes.

The cannulated fixation screw of the invention is preferably used with a guide wire or rod to align and retain the screw for drilling and tapping a bone.

BRIEF DESCRIPTION OF THE DRAWINGS

FIG. 1 is a plan view of a cannulated orthopedic fixation screw according to the invention;

FIG. 2 is a cross sectional taken along line 2—2 of FIG. 1 showing the distal or cutting edge of the screw;

FIG. 3 is a perspective view of the tip and a portion of the shaft of the screw of FIG. 1;

FIG. 4 is a cross-sectional view taken along line 4—4 of FIG. 1 showing the chuck end of the screw according to the invention;

FIG. 5 is a perspective view of the chuck of FIG. 4;

FIG. 6 is a cross sectional view of the chuck of FIG. 5; and

FIG. 7 is a perspective view showing the use of a guide wire to position the screw of FIGS. 1-6 in a bone.

DESCRIPTION OF THE PREFERRED EMBODIMENT

Referring to FIG. 1, a cannulated fixation screw 10 includes a shaft 12, a drilling tip 14, a chuck 16, and threads 18. As best shown in FIGS. 1 and 2, the shaft 12 includes therethrough a cannula 20.

Referring to FIGS. 1, 2 and 3, the drilling tip 14 includes a plurality of flutes 22. The drilling tip may include any desired number of flutes 22; however, the preferred embodiment illustrated includes four such flutes 22. The flutes are formed by the intersection of a cutting face 24 extending radially from the shaft and a second face 26 perpendicular to the cutting face 24.

The flutes 22 define a plurality of lands 28 therebetween with each of the lands 28 including a threaded portion 30 on the shaft 12 and an unthreaded or smooth transition portion 32 adjacent the drilling tip 14. Each of the lands has a heel 34 defined by the intersections of the lands 28 with the second faces 26. The threaded portions 30 are formed such that each thread 18 has a maximum thread height at the cutting faces 24 to define a plurality of acute-angled cutting edges 36. Each thread 18 in the threaded portions 30 tapers from the cutting edge to a minimum thread height at the heels 34 of the lands 28.

As best shown in FIGS. 1 and 3, the smooth portions 32 of the lands 28 form a generally frustoconical shape adjacent the drilling tip 14. The drilling tip 14 comprises a plurality of drilling teeth 38, the drilling teeth 38 being formed at the end of each land 28. The drilling teeth 38 are formed by the intersection of the cutting face 24, the frustoconical smooth portion 32, and the cannula 20.

Referring to FIG. 1, 3 and 7, the drilling teeth 36 are formed such that when the shaft 12 is urged against a bone 40 with sufficient force, rotation of the shaft 12 causes the drilling teeth 38 to drill a passage 42 in the bone 40 so that the shaft 12 may enter into the bone. After the drilling teeth 38 and the smooth transition portions 32 have entered the bone 40, the cutting edges 36 of the threaded portions 30 begin to tap threads into the bone 40. Further rotation of the shaft 12 with application of sufficient force between the shaft 12 and the bone 40 results in simultaneous drilling and tapping of the passage 42 in the bone 40.

Referring to FIG. 4, the chuck 16 may be formed to have any convenient cross section such as square to provide means for attaching the fixation screw 10 to a drilling apparatus (not shown).

Referring to FIGS. 5 and 6, the shaft 12 may alternatively include thereon a generally hemispherical head 44 suitable for engaging the outer surface of a bone 40 when the cannulated fixation screw 10 is to be left in position in the bone 40. The hemispherical head 44 preferably includes therein a generally hexogonal-shaped recess 46 to accommodate ordinary hexogonal drive wrenches (not shown).

The cannulated fixation screw 10 may be formed of any convenient material such as titanium, a titanium alloy or a suitable stainless steel.

As shown in FIG. 7, the cannulated fixation screw is preferably used in conjunction with a guide wire 48. It has been found that an orthopedist or other suitably trained personnel may drill a hole having a relatively small diameter in the bone 40 at a predetermined location with very little error in the location of the hole; whereas it is more difficult to drill a hole at a predetermined location with a relatively large drilling device without the risk of significant error in the location of the hole. Therefore, a relatively small hole 50 is drilled through the bone and the guide wire 48 is inserted therein. The cannulated fixation screw 10 is then inserted over the guide wire 48 and positioned around the guide wire 48 with the drilling teeth 36 being adjacent the bone 40. The guide wire 48 positions the cannulated fixation screw 10 while the drilling teeth drill 38 drill a passage in the bone 40 and the cutting edges 36 tap threads in the passage 40.

The cannulated fixation screw 10 is formed using conventional machining tools and procedures well known in the art. It may be convenient to begin with a cylindrical cannulated shaft 12 having flat ends. The square chuck 16 is formed by machining the sides of the shaft 12 to form the four intersecting planes required to form the square chuck 16.

Secondly, the transition zone 32 is formed as a frustocone, best shown in FIG. 1. The flutes 22 are then machined into the shaft 12, which is then threaded. The threads in the lands 28 are machined to provide relief with the thread height decreasing from the cutting edges 36 to the heels of the lands 28. The shaft 12 is preferably machined so that the diameter of the threaded portion 18 is greater than the unthreaded portion of the shaft 12. Portions of the frustoconical transition zone 32 must be machined away to form the drilling teeth 38.

Although the present invention has been described with reference to a particular embodiment thereof, it will be understood by those skilled in the art that numerous modifications may be made without departing from the scope of the invention. Accordingly, all modifications and equivalents which are properly within the scope of the appended claims are included in the present invention.

What is claimed is:

1. A cannulated fixation screw for use in orthopedic surgery comprising;

an elongate hollow shaft defining a cannula through the center of the shaft;

self-tapping threads adjacent the distal end of the shaft formed by a plurality of flutes arcuately spaced apart around the circumference of the shaft having lands therebetween, each of said lands having a plurality of threads thereon and a heel, the flutes forming a plurality of self-tapping cutting edges on each of said threads, each thread having a maximum thread height at the cutting edge thereof, and a mimimum thread height at the heel of the land in which the thread is located; and means on the distal tip forming a plurality of teeth projecting from said distal tip, each of said teeth forming a drilling edge formed by the intersection of the cutting face of the corresponding land, the cannula and the exterior of the corresponding land.

* * * * *